United States Patent [19]

Ninger et al.

[11] Patent Number: 4,663,316

[45] Date of Patent: May 5, 1987

[54] ANTIBIOTIC CLATHRATES AND PHARMACEUTICAL COMPOSITIONS THEREOF

[75] Inventors: Fred C. Ninger, Secaucus; Weichi Liao, Iselin, both of N.J.

[73] Assignee: Warner-Lambert Company, Morris Plains, N.J.

[21] Appl. No.: 750,718

[22] Filed: Jun. 28, 1985

[51] Int. Cl.$^4$ ........................ A61K 31/665; C07F 9/09
[52] U.S. Cl. .................................... 514/99; 514/778; 536/103; 549/204; 549/222
[58] Field of Search ................ 549/204, 222; 536/103; 514/778, 99

[56] References Cited

U.S. PATENT DOCUMENTS 4,578,383  3/1986  Stampwala et al. ................ 549/222

Primary Examiner—Richard L. Raymond
Attorney, Agent, or Firm—Sandra M. Person; Ronald A. Daignault

[57] ABSTRACT

Cyclodextrin clathrates of certain unsaturated phosphorous containing antibiotics exhibit enhanced stability in pharmaceutical compositions.

10 Claims, No Drawings

ANTIBIOTIC CLATHRATES AND PHARMACEUTICAL COMPOSITIONS THEREOF

BACKGROUND

The compound designated phosphotrienin is a phosphorus containing antibiotic produced by cultivating a specific strain streptomycetes which produces the compound. It has antifungal and antitumor activity. The compound's structural formula is:

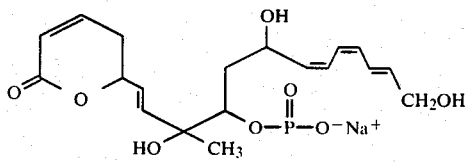

This compound is also called pyranophosphate and identified as CL1565A.

Due to the presence of a molecular triene configuration, phosphotrienin undergoes rapid oxidative degradation in oxygen-containing environments. Its instability increases with increasing temperatures. In view of its pronounced instability, its pharmacological and clinical evaluation appeared severely restricted unless a mechanism could be found to stabilize phosphotrienin to permit its use in formulating suitable dosage forms such as solutions and/or dry products such as tablets or capsules.

THE INVENTION

It has been discovered that phosphotrienin can be stabilized against oxidative degradation by reacting it with various cyclodextrins to form inclusion compounds or clathrates. Specifically, the conjugated triene group therein, is entrapped in the cavity of a cyclodextrin molecule and is thus protected by the shielding effect of the cyclodextrin from oxygen and/or other free radicals.

It has been found that due to the hydrophobic nature of the conjugated triene side chain, cyclodextrins have a higher affinity for this unsaturated side chain than for the other functional groups on the phosphotrienin molecule. In addition, the molecular dimensions estimated for the cavity of cyclodextrin and the corresponding triene group of phosphotrienin are compatible for the formation of clathrates.

Pharmaceutical preparations containing the clathrates of the invention exhibit the antibiotic, antifungal, and antitumor properties of phosphotrienin, but do not exhibit its oxidative instability.

ADVANTAGES OF THE INVENTION

The phosphotrienin clathrate products made in accordance with the invention have several advantages over the parent compound from which they are derived. The steric protection of phosphotrienin through cyclodextrin clathrate formation provides, due to the good stability of cyclodextrins, a shield for the oxidation-prone triene group. Additional protection to another functional group, the lactone ring, is possible when specific cyclodextrins having larger cavities are used.

Other aspects and advantages of the invention will become apparent after considering the following description and claims.

DESCRIPTION OF THE INVENTION

In its broadest aspects, the invention provides:

(1) cyclodextrin clathrates of the antibiotic phosphotrienin which compound has the structural formula set out above.

(2) pharmaceutical compositions containing one or more of the clathrates of (1) above.

Phosphotrienin

The compound, i.e., compound CL1565A or pyranophosphate is made by the cultivation of a specific strain of streptomycetes.

The production and use of phosphotrienin and its salts are described in U.S. application Ser. No. 627,367, filed July 2, 1984, now U.S. Pat. No. 4,578,383, which is a C-I-P of Ser. No. 447,544, filed Dec. 7, 1982, which is a C-I-P of Ser. No. 439,973, filed Nov. 8, 1982 and now abandoned, and Ser. No. 351,704, filed Feb. 24, 1982, and now abandoned. These disclosures are herewith incorporated for reference. All of these applications were assigned to the assignee of the instant application.

In general, the production and recovery of phosphotrienin is carried out using well-known techniques.

CYCLODEXTRIN

The cyclodextrins useful in complexing or clathrating the antibiotic compound discussed above include most forms of cyclodextrin. One or more of the alpha-, beta-, gamma-, or delta-forms of cyclodextrin and various equivalents thereof can be employed. The *Merck Index*, 10th edition (1983), outlines the properties of several cyclodextrins on pages 389-90 (No. 2712).

REACTION PROCEDURE

The complexing reaction, or clathration, between phosphotrienin and one or more cyclodextrins follows procedures which are generally well known and customarily used for the production or such inclusion compounds. Parameters such as temperature and pressure vary and depend upon solvents used and the physical characteristics of the reactants.

It is generally preferred to react aqueous or organic solvent solutions of phosphotrienin with an aqueous solution of the cyclodextrin. To insure proper reaction, it is preferred that the organic solvent used be miscible with water.

The use of heat is usually not necessary.

The clathrates produced in solution are recovered by conventional techniques, e.g., solvent evaporation, and/or lyophilization. Other conventional separation and purification techniques can be used instead of, or in combination with, these techniques.

It should be noted that the clathrate complexes produced in accordance with the invention are useful not only per se, but also in combination with numerous diluents and excipients. For example, the use of excipients, carriers, diluents and other additives conventionally employed in the preparation of pharmaceutical dosage forms is contemplated.

The cyclodextrin clathrates produced herein are useful in a wide variety of pharmaceutical dosage forms. Phosphotrienin clathrates in aqueous solvents and/or other suitable solvents may be injected intravenously. Tablets, capsules, caplets, and other solid forms can be used to prepare oral dosage forms. Creams, lotions and other suitable forms may be formulated for topical administration.

The preferred process for producing the clathrate compounds is illustrated in the following examples.

EXAMPLE 1

750 mg of the monosodium salt of phosphotrienin was dissolved in 90 ml of water in which 0.8 g of alpha-cyclodextrin was dissolved. The final volume was then made to 100 ml. The clathrate form of phosphotrienin with alpha-cyclodextrin was estimated at about 43% in the solution after reaction.

EXAMPLE 2

1.6 g of alpha-cyclodextrin was dissolved in 90 ml of water, 750 mg of the monosodium salt of phosphotrienin was added and dissolved. The final volume was made to 100 ml. 75% of the phosphotrienin was estimated in the clathrate form with alpha-cyclodextrin in this solution was after reaction.

EXAMPLE 3

8.0 g of alpha-cyclodextrin was dissolved in 90 ml of water, 750 mg of the monosodium salt of phosphotrienin was added and dissolved. The final volume was made to 100 ml. The active compound was phosphotrienin was estimated at 95% as the clathrate with alpha-cyclodextrin in this solution after reaction.

EXAMPLE 4

Solutions obtained in Examples 1, 2 and 3 were lyophilized. The percentage of active compound in the clathrate form was estimated to be 50%, 100% and 100% respectively in the lyophilized powder.

EXAMPLE 5, 6, 7

Instead of using water as a solvent as given in Examples 1, 2 and 3, a 60% aqueous ethanol was used as an alternate solvent. The application of vacuum and subsequent drying at 34°–40° C., or the application of lyophilization produced a white powder of alpha-cyclodextrin clathrate of phosphotrienin.

EXAMPLE 8

1.88 g of beta-cyclodextrin was dissolved in 200 ml. of water; 750 mg of the monosodium salt of phosphotrienin was added and dissolved. The solution was lyophilized to produce a powder of the beta-cyclodextrin clathrate of phosphotrienin.

EXAMPLE 9

750 mg of the monosodium salt of phosphotrienin is dissolved in 100 ml of water containing 2.15 g of gamma-cyclodextrin. The solution was lyophilized to produce a powder of the gamma-cyclodextrin clathrate of phosphotrienin.

EXAMPLE 10

750 mg of the monosodium salt of phosphotrienin is dissolved in 100 ml of water containing 2.42 g of deltacyclodextrin. The solution was lyophilized to produce a powder of delta-cyclodextrin clathrate of phosphotrienin.

The equilibrium constant for the clathrate formation between phosphotrienin and alpha-cyclodextrin was measured in an aqueous buffer solution of pH 6. This constant was employed to estimate the extent of clathrate formation in Examples 1, 2, 3 and 4.

Thermal stability tests confirmed the excellent stabilities of the clathrate compounds compared with original phosphotrienin. The results of the thermal stability test via HPLC assay of cyclodextrin clathrate of phosphotrienin s shown below:

| Lyophilized Powder | % Remaining (at 25° C.) |
|---|---|
| phosphotrienin | 70% (after 5 weeks) |
| Alpha-cyclodextrin clathrate of CL1565A | 100% (after 4 weeks) |

The following examples illustrate the preferred methods of using the clathrate compounds of this invention in pharmaceutical dosage forms.

EXAMPLE 11

Phosphotrienin alpha-cyclodextrin Solutions for Injection

Solutions in Examples 1, 2 and 3 were prepared and divided into ampoules under sterile manufacturing conditions such that each ampoule contains the required dose for therapeutic indications. Each ampoule was flushed with nitrogen gas and sealed.

EXAMPLE 12

Phosphotrienin alpha-cyclodextrin Lyophilized Powder for Injection

Solutions in Examples 1, 2 and 3 were prepared and divided into vials under sterile manufacturing conditions that each vial contains a suitable dose for therapeutic activity. Lyophilization was carried out to remove the water and obtain a white powder. Each vial was capped and sealed. This was useful as an injection with the addition of normal saline solution for injection.

Reasonable variations, such as those which would occur to a skilled artisan, can be made herein without departing from the scope of the invention.

We claim:

1. Cyclodextrin clathrates of the antibiotic compound of phosphotrienin having the structural formula:

$$\text{structural formula with } O-P-O^-Na^+, OH, CH_2OH, CH_3, HO \text{ groups}$$

2. The alpha-cyclodextrin clathrate of the compound of claim 1.

3. The beta-cyclodextrin clathrate of the compound of claim 1.

4. The gamma-cyclodextrin clathrate of the compound of claim 1.

5. The delta-cyclodextrin clathrate of the compound of claim 1.

6. A pharmaceutical composition containing one or more of the clathrates of claim 1 and a pharmaceutically acceptable carrier.

7. A pharmaceutical composition containing the clathrate of claim 2 and a pharmaceutically acceptable carrier.

8. A pharmaceutical composition containing the clathrate of claim 3 and a pharmaceutically acceptable carrier.

9. A pharmaceutical composition containing the clathrate of claim 4 and a pharmaceutically acceptable carrier.

10. A pharmaceutical composition containing the clathrate of claim 5 and a pharmaceutically acceptable carrier.

* * * * *